(12) United States Patent
Chauveau et al.

(10) Patent No.: US 7,067,149 B1
(45) Date of Patent: *Jun. 27, 2006

(54) FAST DISINTEGRATING TABLET

(75) Inventors: Charles Chauveau, Valbonne (FR); Jean-Marc Zuccarelli, Antibes (FR); Nourredine Nouri, Cannes (FR); Maryvonne Barbero, Antibes (FR)

(73) Assignee: Ethypharm, Houdan (FR)

( * ) Notice: Subject to any disclaimer, the term of this patent is extended or adjusted under 35 U.S.C. 154(b) by 0 days.

This patent is subject to a terminal disclaimer.

(21) Appl. No.: 09/830,946

(22) PCT Filed: Nov. 3, 1999

(86) PCT No.: PCT/FR99/02681

§ 371 (c)(1), (2), (4) Date: Aug. 22, 2001

(87) PCT Pub. No.: WO00/27357

PCT Pub. Date: May 18, 2000

(30) Foreign Application Priority Data

Nov. 6, 1998  (FR) .................................. 98 14034

(51) Int. Cl.
*A61K 9/20* (2006.01)
*A61K 9/14* (2006.01)

(52) U.S. Cl. ...................... 424/465; 424/464; 424/489; 514/960; 514/951

(58) Field of Classification Search ................ 424/400, 424/441, 465, 470, 46, 464, 489, 490, 493, 424/494, 497; 514/951, 960, 961
See application file for complete search history.

(56) References Cited

U.S. PATENT DOCUMENTS

| 4,832,956 | A | * | 5/1989 | Gergely et al. ............. 424/466 |
| 5,064,656 | A | * | 11/1991 | Gregely et al. ............. 424/463 |
| 5,215,755 | A | | 6/1993 | Roche et al. |
| 5,567,439 | A | * | 10/1996 | Meyers et al. ............... 424/486 |
| 5,869,098 | A | * | 2/1999 | Misra et al. ................. 424/484 |
| 5,876,759 | A | * | 3/1999 | Gowan, Jr. .................. 424/494 |
| 5,958,453 | A | * | 9/1999 | Ohno et al. ................. 424/465 |
| 5,994,348 | A | * | 11/1999 | Ku et al. .................. 514/223.5 |
| 6,099,865 | A | * | 8/2000 | Augello et al. ............. 424/494 |
| 6,465,009 | B1 | * | 10/2002 | Liu et al. .................... 424/464 |

* cited by examiner

*Primary Examiner*—Sreeni Padmanabhan
*Assistant Examiner*—Sharmila Gollamudi
(74) *Attorney, Agent, or Firm*—Caesar, Rivise, Bernstein, Cohen & Pokotilow, Ltd.

(57) ABSTRACT

The invention concerns an improved multiparticulate tablet disintegrating in the mouth in contact with saliva in less than 40 seconds. The invention is characterized in that it is based on particles of coated active principle, said particles having intrinsic compression properties and a mixture of carriers, the proportion of carrier mixture relative to coated active principle particles being 0.4 to 6 parts by weight, the carrier mixture comprising: a disintegrating agent; a diluting soluble agent with binding properties; a lubricant; a permeabilizing agent; and advantageously lubricants, sweeteners, flavoring and coloring agents, the proportion of disintegrating agent and soluble agent relative to the tablet mass being 1 to 15% by weight for the former and 30 to 90% by weight for the latter.

7 Claims, No Drawings

FAST DISINTEGRATING TABLET

The invention relates to a rapidly disintegratable tablet of the type which disintegrates in the mouth in less than 40 seconds, said tablet comprising particles of coated active principle which have intrinsic compression characteristics, and a mixture of excipients.

Ibuprofen, paracetamol and aspirin may be mentioned as examples of active principles which can be used to produce the tablets according to the invention.

Tablets based on ibuprofen are already known.

Thus patent U.S. Pat. No. 5,215,755 describes chewing tablets in which the ibuprofen is present in the form of granules having a coating based on hydroxyethyl cellulose or a hydroxyethyl cellulose/hydroxypropyl methyl cellulose mixture. This coating was chosen to overcome the observed deficiencies of the coatings of the prior art based on ethyl cellulose only.

The object of the invention is to provide tablets obtained with the aid of particles of coated active principle which not only disintegrate rapidly in the mouth in less than 40 seconds, but also have a pleasant palatability, together with satisfactory hardness characteristics enabling them to be manufactured industrially, and which keep sufficiently well under normal storage conditions to enable them to be handled by the patient, these tablets also optimizing the bioavailability of the active principle.

The tablet according to the invention is characterized in that it is based on particles of coated active principle which have intrinsic compression characteristics, and on a mixture of excipients, the ratio of excipient mixture to coated active principle being 0.4 to 6 parts by weight, preferably 1 to 4 parts by weight, the mixture of excipients comprising:

a disintegration agent;

a soluble diluent agent with binding properties which consists of a polyol having less than 13 carbon atoms and being either in the form of the directly compressible product with an average particle diameter of 100 to 500 µm, or in the form of a powder with an average particle diameter of less than 100 µm, this polyol preferably being selected from the group comprising mannitol, xylitol, sorbitol and maltitol, it being understood that sorbitol cannot be used alone and that, in the case where there is only one soluble diluent agent with binding properties, it is used in the form of the directly compressible product, whereas in the case where there are at least two soluble diluent agents with binding properties, one is present in the directly compressible form and the other is present in powder form, it then being possible for the polyols to be the same, the ratio of directly compressible polyol to powder polyol being 99/1 to 20/80, preferably 80/20 to 20/80;

a lubricant;

a permeabilizing agent; and advantageously sweeteners, flavourings and colours, the proportion of disintegrating agent being 1 to 15% by weight, preferably 2 to 7% by weight, and the proportion of soluble agent being 30 to 90% by weight, preferably 40 to 70% by weight, based in each case on the weight of the tablet.

The soluble diluent agent with binding properties consists of a polyol having less than 13 carbon atoms and being either in the form of the directly compressible product with an average particle diameter of between 100 and 500 micrometres, or in the form of a powder with an average particle diameter of less than 100 micrometres, this polyol preferably being selected from the group comprising mannitol, xylitol, sorbitol and maltitol, it being impossible to use sorbitol alone.

If there is a single soluble diluent agent with binding properties, therefore different from sorbitol, it is used in the form of the directly compressible product.

If at least two soluble diluent agents with binding properties are used, one is present in the form of the directly compressible product and the other, which can consist of the same polyol, is present in the form of a powder in which the average diameter of the constituent particles is less than 100 micrometres, the ratio of directly compressible polyol to powder polyol being 99/1 to 20/80, preferably 80/20 to 20/80.

The disintegration agent is selected from the group comprising especially crosslinked sodium carboxymethyl cellulose (known in the profession as croscarmellose), crospovidone and mixtures thereof. By virtue of the choice and proportion of this disintegration agent, the tablet retains an acceptable hardness for normal handling conditions when tablets are kept in leaktight packaging up to temperatures of at least 30° C.

The chosen proportions of disintegration agent and soluble agent for constituting the excipient are 1 to 15% by weight and 30 to 90% by weight, respectively, based in each case on the weight of the tablet.

The lubricant preferably used in this mixture of excipients is selected from the group comprising magnesium stearate, sodium stearyl fumarate, stearic acid, micronized polyoxyethylene glycol (micronized Macrogol 6000) and mixtures thereof. It can be used in a proportion of 0.05 to 2%, based on the total weight of the tablet.

The permeabilizing agent used is a compound selected from the group comprising especially silicas with a high affinity for aqueous solvents, such as the precipitated silica better known by the trade mark Syloid®, maltodextrins, β-cyclodextrins and mixtures thereof.

The permeabilizing agent allows the creation of a hydrophilic network which facilitates the penetration of the saliva and hence assists the disintegration of the tablet.

In one highly advantageous embodiment of the tablets according to the invention, the permeabilizing agent is the precipitated silica better known by the trade mark Syloid® FP244. In fact, this silica not only assists the disintegration of the tablets, but also, through its properties as a flow promoter, favours the rearrangements of the particles during compression, and it makes it possible on the one hand to reduce the amount of hydrophobic lubricant needed to ensure optimum manufacturing conditions, and on the other hand to reduce the intensity of the compression force needed to produce a tablet which can be handled under these industrial conditions.

The proportion of permeabilizing agent is between 0.5 and 5% by weight, based on the weight of the tablet.

A sweetener and optionally a flavouring and a colour are also included in the mixture of excipients forming part of the composition of the tablets according to the invention.

The sweetener can be selected from the group comprising especially aspartame, potassium acesulfame, sodium saccharinate, neohesperidin dihydrochalcone and mixtures thereof.

The flavourings and colours are those conventionally used in pharmacy for the preparation of tablets.

Compared with the already existing tablets of the type in question, the tablets according to the invention have an improved palatability and particularly an improved taste and texture, and can allow a reduction in the ratio of tablet weight to active principle dose.

They have a satisfactory hardness, enabling them to be handled under standard operating conditions without special operating precautions. By way of indication, it is pointed out that hardnesses which satisfy these conditions are generally between 20 and 70 Newtons.

The tablets according to the invention can be prepared in the following manner or by any other appropriate process. Particles of coated active principle which have intrinsic compression characteristics are added to a mixture of excipients containing a disintegration agent, a soluble diluent agent with binding properties, a permeabilizing agent and advantageously a lubricant, sweeteners, flavourings and colours, in the proportions indicated above. The mixture obtained in this way is homogenized in a dry mixer and then subjected to a compression force which gives the resulting tablet a satisfactory hardness, enabling it to be manufactured industrially and handled under normal conditions without special operating precautions; by way of indication, it is pointed out that hardnesses which satisfy these conditions are generally between 20 and 70 Newtons.

EXAMPLES

Example 1

Tablet Containing 200 mg of Ibuprofen

Table I shows the unit formula and the centesimal formula of this tablet.

TABLE I

| Constituents | Unit formula | Centesimal formula |
| --- | --- | --- |
| Coated ibuprofen granules | 261.70 | 37.24 |
| Granulated mannitol | 186.65 | 26.71 |
| Pulverulent mannitol | 186.65 | 26.76 |
| Croscarmellose | 21.00 | 3.00 |
| Precipitated silica | 7.00 | 1.00 |
| Aspartame | 9.60 | 1.37 |
| Potassium acesulfame | 6.40 | 0.91 |
| Lemon flavouring | 16.00 | 2.29 |
| Mint flavouring | 2.00 | 0.29 |
| Magnesium stearate | 3.00 | 0.43 |
| | 700.00 mg | 100.00 |

This tablet is prepared as indicated below.

The excipients identified in Table I are sieved on a grid with a mesh size of 1000 μm.

The different constituents are weighed in separate containers of appropriate capacity.

The coated ibuprofen particles (having the formulation given in Table II below), the granulated mannitol, the pulverulent mannitol, the croscarmellose, the aspartame, the potassium acesulfame, the precipitated silica and the flavourings are introduced into a rotating mixer.

A homogeneous mixture is prepared.

The mixer is stopped, the magnesium stearate is added and the mixing operation is continued for 1 to 5 min, according to the weight of mixture.

The mixture obtained is compressed on a rotary machine to give tablets with the following characteristics:

average weight of between 665 mg and 735 mg;

breaking strength of between 20 and 50 N; and average disintegration time in the mouth of less than 40 seconds.

This disintegration time corresponds to the time between the moment when the tablet is placed in contact with the saliva in the mouth and the moment when the suspension resulting from the disintegration of the tablet in contact with the saliva is swallowed.

TABLE II

| Formula of coated ibuprofen granules | |
| --- | --- |
| Ibuprofen | 200.00 |
| Ethyl cellulose | 40.00 |
| Precipitated silica | 13.70 |
| Hydroxypropyl methyl cellulose | 8.00 |
| | 261.70 mg |

Example 2

Tablet Containing 500 mg of Aspirin

Table III shows the unit formula and the centesimal formulation of this tablet.

TABLE III

| Constituents | Unit formula | Centesimal formula |
| --- | --- | --- |
| Coated aspirin granules | 564.00 | 40.26 |
| Granulated mannitol | 333.00 | 23.77 |
| Pulverulent mannitol | 333.00 | 23.77 |
| Crospovidone | 120.00 | 8.57 |
| Precipitated silica | 14.00 | 1.00 |
| Aspartame | 14.40 | 1.03 |
| Potassium acesulfame | 9.60 | 0.69 |
| Lemon flavouring | 5.00 | 0.36 |
| Sodium stearyl fumarate | 7.00 | 0.50 |
| | 1400.00 mg | 99.928622 |

The tablets are prepared in the same way as in Example 1 with the aid of coated granules having the formula given in Table IV below.

TABLE IV

| Formula of coated aspirin granules | |
| --- | --- |
| Aspirin | 500.0 |
| Ethyl cellulose | 50.0 |
| Hydroxypropyl methyl cellulose | 10.0 |
| Colloidal silica | 4.0 |
| | 564.0 mg |

Example 3

Tablet Containing 500 mg of Paracetamol

Table V shows the unit formula and the centesimal formula of this tablet.

TABLE V

| Constituents | Unit formula | Centesimal formula |
| --- | --- | --- |
| Coated paracetamol granules | 566.50 | 40.44 |
| Granulated mannitol | 331.30 | 23.65 |
| Pulverulent mannitol | 331.30 | 23.65 |
| Crospovidone | 120.00 | 8.57 |
| Precipitated silica | 14.00 | 1.00 |
| Aspartame | 19.20 | 1.37 |
| Potassium acesulfame | 12.80 | 0.91 |

TABLE V-continued

| Constituents | Unit formula | Centesimal formula |
|---|---|---|
| Blackcurrant flavouring | 5.00 | 0.36 |
| Magnesium stearate | 0.90 | 0.06 |
| | 1401.00 mg | 100.00 |

The tablets are prepared in the same way as in Example 1 with the aid of coated granules having the formula given in Table VI below.

TABLE VI

| Formula of coated paracetamol granules | |
|---|---|
| Paracetamol | 500.0 |
| 30% dispersion of poly(ethyl acrylate/methyl methacrylate) | 17.0 |
| Aminoalkyl methacrylate copolymer | 33.0 |
| Precipitated silica | 16.5 |
| | 566.5 mg |

The invention claimed is:

1. Improved multiparticulate tablet which disintegrates in contact with the saliva in the mouth in less than 40 seconds, comprising particles of coated active substance and a mixture of excipients being free of effervescent agents, the ratio of excipient mixture to coated active substance particles being 0.4 to 6 parts by weight, the mixture of excipients comprising 1 to 15% by weight based on the weight of the tablet of a disintegration agent selected from the group consisting of croscarmellose, crospovidone and mixtures thereof; 30 to 90% by weight, based on the weight of the tablet of a at least two soluble diluent agents with binding properties which consists of a polyol selected from the group consisting of mannitol, xylitol, sorbitol and maltitol and at least one diluent agent being in the form of the directly compressible product with an average particle diameter of 100 to 500 μm, and at least diluent agent being in the form of a powder with an average particle diameter of less than 100 μm, the ratio of directly compressible polyol to powder polyol being 99/1 to 20/80; 0.05 to 2% by weight based on the weight of the tablet of a lubricant selected from the group consisting of magnesium stearate, sodium stearyl fumarate, steriac acid, micronized polyoxyethylene glycol and mixtures thereof; at least one from the group consisting of sweeteners, flavorings, colors and mixtures thereof; and 0.1 to 10% by weight based on the weight of the tablet of a permeabilizing agent selected from the group consisting of precipitated silicas with a high affinity for aqueous solvents, maltodextrins, β-cyclodextrines and mixtures thereof.

2. Improved multiparticulate tablet according to claim 1, wherein the ratio of excipient mixture to coated active substance is 1 to 4 parts by weight.

3. Improved multiparticulate tablet according to claim 1, wherein the proportion of directly compressible polyol to powder polyol is 80/20 to 20/80.

4. Tablet according to claim 1, wherein the proportion of disintegration agent is 2 to 7% by weight and the proportion of soluble agent is 40 to 70% based in each case on the weight of the tablet.

5. Tablet according to claim 1, wherein the active substance is selected from the group consisting of aspirin, paracetamol and ibuprofen.

6. Tablet according to claim 1, wherein the proportion of permeabilizing agent is 0.5 to 5% based on the weight of the tablet.

7. Tablet according to claim 1, wherein the sweetener is selected from the group consisting of aspartame, potassium acesulfame, sodium saccharinate, neohesperidin dihydrochalcone and mixtures thereof.

* * * * *